United States Patent
Kawakami et al.

(10) Patent No.: US 9,592,517 B2
(45) Date of Patent: Mar. 14, 2017

(54) FLUID EJECTION DEVICE SYSTEM AND MEDICAL APPARATUS

(71) Applicant: SEIKO EPSON CORPORATION, Tokyo (JP)

(72) Inventors: Daisuke Kawakami, Matsumoto (JP); Hirokazu Sekino, Chino (JP); Atsuya Hirabayashi, Chino (JP)

(73) Assignee: Seiko Epson Corporation, Tokyo (JP)

(*) Notice: Subject to any disclaimer, the term of this patent is extended or adjusted under 35 U.S.C. 154(b) by 162 days.

(21) Appl. No.: 13/765,589

(22) Filed: Feb. 12, 2013

(65) Prior Publication Data
US 2013/0214058 A1  Aug. 22, 2013

(30) Foreign Application Priority Data

Feb. 17, 2012 (JP) ................... 2012-032462
Apr. 6, 2012 (JP) ................... 2012-087125

(51) Int. Cl.
| | |
|---|---|
| *A61B 17/3203* | (2006.01) |
| *B05B 3/00* | (2006.01) |
| *B05B 7/04* | (2006.01) |
| *B05B 12/06* | (2006.01) |
| *A61B 17/00* | (2006.01) |

(52) U.S. Cl.
CPC ............ *B05B 3/00* (2013.01); *A61B 17/3203* (2013.01); *A61B 90/98* (2016.02); *B05B 7/0408* (2013.01); *B05B 12/06* (2013.01); *A61B 2017/00017* (2013.01); *A61B 2090/0806* (2016.02); *A61B 2090/0807* (2016.02)

(58) Field of Classification Search
CPC .... B05B 1/08; B05B 3/04; B05B 7/12; B05B 3/00; A01G 27/00; A61B 17/3203; A61B 2017/00154
USPC ....... 239/67, 68, 70, 102.1, 102.2, 397, 407, 239/413
See application file for complete search history.

(56) References Cited

U.S. PATENT DOCUMENTS 7,628,339 B2 * 12/2009 Ivri et al. ................ 239/102.2
7,901,374 B2   3/2011 Seto et al.
8,177,918 B2 *  5/2012 Schmitt ................... 134/169 R
(Continued)

FOREIGN PATENT DOCUMENTS

| JP | 2008-82202 | 4/2008 |
|---|---|---|
| JP | 2010-082056 | 4/2010 |
| JP | 3172382 | 11/2011 |

*Primary Examiner* — Arthur O Hall
*Assistant Examiner* — Christopher R Dandridge
(74) *Attorney, Agent, or Firm* — Workman Nydegger

(57) ABSTRACT

A fluid ejection device system includes: a fluid ejecting unit configured to change a volume of a fluid chamber to thereby eject fluid from a nozzle provided at a distal end of a fluid ejection pipe connected to the fluid chamber; a fluid supplying unit connected to the fluid ejecting unit by a connection tube and configured to supply the fluid to the fluid chamber; a control unit configured to control operation of the fluid ejecting unit and the fluid supplying unit; and a stand configured to hold at least a part of the fluid ejecting unit, and when it is detected that the fluid ejecting unit is held in the stand, the control unit controls at least one of the fluid ejecting unit and the fluid supplying unit to thereby execute a predetermined discharge operation for discharging the fluid in the fluid chamber.

12 Claims, 6 Drawing Sheets

(56) References Cited

U.S. PATENT DOCUMENTS

| | | | | |
|---|---|---|---|---|
| 8,857,734 | B2* | 10/2014 | Kojima | B05B 1/08 |
| | | | | 239/102.1 |
| 9,277,934 | B2* | 3/2016 | Kojima | A61B 17/3203 |
| 2006/0184166 | A1* | 8/2006 | Valle | A61B 18/14 |
| | | | | 606/41 |
| 2007/0163575 | A1* | 7/2007 | Rojas, Jr. | A61M 11/06 |
| | | | | 128/200.21 |
| 2007/0295328 | A1* | 12/2007 | Raghuprasad | 128/200.21 |
| 2010/0079522 | A1 | 4/2010 | Seto et al. | |
| 2011/0036859 | A1* | 2/2011 | Matsuzaki et al. | 222/1 |
| 2011/0087189 | A1* | 4/2011 | Jacobson et al. | 604/506 |
| 2014/0346245 | A1* | 11/2014 | Van Der Sluis | A61M 11/005 |
| | | | | 239/4 |

* cited by examiner

FLUID EJECTION DEVICE SYSTEM AND MEDICAL APPARATUS

BACKGROUND

1. Technical Field

The present invention relates to a fluid ejection device system for ejecting fluid from a nozzle to treat a biological tissue.

2. Related Art

There is proposed a fluid ejection device for ejecting fluid such as water and physiological saline from a nozzle in a pulse-like manner to thereby perform excision, incision, and the like of a biological tissue (see, for example, JP-A-2008-82202). When a surgical operation is performed using the fluid ejection device, it is possible to perform the surgical operation without thermally damaging the biological tissue or damaging tissues such as blood vessels and nerves.

The fluid ejection device supplies the fluid to a fluid chamber using a supply pump and reduces the volume of the fluid chamber to pressurize the fluid to thereby eject the fluid from the nozzle in a pulse-like manner. Therefore, the fluid chamber needs to be filled with the fluid. If air bubbles are mixed in the fluid chamber, the fluid cannot be ejected. Therefore, when the use of the fluid ejection device is started, initial filling work for filling the fluid chamber with the fluid is necessary. Thereafter, air bubble discharge work for discharging the air bubbles in the fluid chamber needs to be performed as appropriate.

However, in the initial filling work and the air bubble discharge work, an operator holds the fluid ejection device and adjusts an ejection amount and the like while directing the fluid to be ejected to a container in which the fluid can be stored. Therefore, the operator is burdened with the work.

SUMMARY

An advantage of some aspects of the invention is to provide a technique and a fluid ejection device system capable of reducing a burden on an operator of a fluid ejection device.

The invention can be implemented as the following forms or application examples.

APPLICATION EXAMPLE 1

This application example is directed to a fluid ejection device system including: a fluid ejecting unit configured to change the volume of a fluid chamber to thereby eject fluid from a nozzle provided at the distal end of a fluid ejection pipe connected to the fluid chamber; a fluid supplying unit connected to the fluid ejecting unit by a connection tube and configured to supply the fluid to the fluid chamber; a control unit configured to control the operation of the fluid ejecting unit and the fluid supplying unit; and a stand configured to hold at least a part of the fluid ejecting unit. The fluid ejecting unit includes a held-state detecting unit for detecting that the fluid ejecting unit is in a held state in which the fluid ejecting unit is held by the stand. When it is detected that the fluid ejecting unit is in the held state, the control unit controls at least one of the fluid ejecting unit and the fluid supplying unit to thereby execute a predetermined discharge operation for discharging the fluid in the fluid chamber.

According to this application example, the stand is provided that holds the fluid ejecting ejection when an operator does not hold the fluid ejecting unit. In other words, the stand houses the fluid ejecting unit when the fluid ejecting unit is temporarily not used. When the fluid ejecting unit is held by the stand, it is detected with the held-state detecting unit of the fluid ejecting unit that the fluid ejecting unit is in a state in which the fluid ejecting unit is held by the stand (the held state). In response to the detection, the control unit controls at least one of the fluid ejecting unit or the fluid supplying unit to execute the predetermined discharge operation for discharging the fluid in the fluid chamber.

When the fluid ejecting unit is held by the stand, the predetermined discharge operation for discharging the fluid in the fluid chamber is automatically executed. Therefore, even if gas is present in the fluid chamber, the gas is discharged together with the fluid. Consequently, since the operator does not need to perform work for discharging the gas in the fluid chamber, it is possible to reduce a burden on the operator. Further, if the fluid ejecting unit is held by the stand when the operator does not hold the fluid ejecting unit (does not perform ejection of the fluid), the predetermined discharge operation for discharging the fluid in the fluid chamber is performed before the operator holds the fluid ejecting unit and performs ejection of the fluid next time. As a result, it is possible to always perform ejection of the fluid in a state in which the gas in the fluid chamber is discharged.

APPLICATION EXAMPLE 2

This application example is directed to the fluid ejection device system according to the application example described above, wherein when it is detected that the fluid ejecting unit is in the held state, the control unit causes the fluid ejecting unit and the fluid supplying unit to operate for a predetermined first time under a predetermined first condition to thereby execute the discharge operation.

According to this application example, if the first condition and the first time are appropriately set, it is possible to perform the initial filling work and use the fluid ejection device when the fluid ejecting unit is held by the stand.

APPLICATION EXAMPLE 3

This application example is directed to the fluid ejection device system according to the application example described above, wherein after causing the fluid ejecting unit and the fluid supplying unit to operate for the predetermined first time, the control unit causes the fluid supplying unit to operate for a predetermined second time under a predetermined second condition, under which the fluid having a flow rate smaller than a flow rate under the first condition is supplied, to thereby execute the discharge operation.

According to this application example, if the first condition and the first time are appropriately set, the fluid discharge work involving air bubble discharge is performed when the fluid ejecting unit is held by the stand. Therefore, it is possible to discharge air bubbles mixed in the fluid chamber.

APPLICATION EXAMPLE 4

This application example is directed to the fluid ejection device system according to the application example described above, wherein a holding-information retaining section for retaining holding information indicating that the fluid ejecting unit is held by the stand is provided in at least one of the fluid ejecting unit and the stand, the fluid ejecting unit includes an initial-held-state detecting unit for detecting, when the fluid ejecting unit is held by the stand, on the basis of the holding information, whether the fluid ejecting unit is in an initial held state in which the fluid ejecting unit is held by the stand for the first time, and when it is detected that the fluid ejecting unit is not in the initial held state, the control unit causes the fluid supplying unit to operate for a predetermined second time under a predetermined second condition, under which the fluid having a flow rate smaller than a flow rate in the first condition is supplied, to thereby execute the discharge operation.

According to this application example, when the fluid ejecting unit is in the initial held state, the fluid is supplied to the fluid chamber for the predetermined second time under the second condition under which the flow rate of the fluid is larger than the flow rate under the predetermined first condition. Therefore, it is possible to perform work for filling the fluid chamber with the fluid (the initial filling work). Once the fluid ejecting unit is held by the stand and the initial filling work is performed, the initial filling work is not performed thereafter. Therefore, when it is attempted to perform the initial filling work, it is necessary to prepare a stand that has not held the fluid ejecting unit at all (an unused stand). As a result, a situation in which the fluid ejecting unit is held by a used stand is prevented. It is possible to keep the fluid ejecting unit clean.

APPLICATION EXAMPLE 5

This application example is directed to the fluid ejection device system according to the application example described above, wherein the fluid ejection device system further includes a suction unit configured to suck the fluid ejected from the fluid ejecting unit, the stand holds at least a part of the fluid ejecting unit when the fluid ejection pipe is inserted into the stand, the fluid ejecting unit includes a suction pipe provided integrally with the fluid ejection pipe, having a suction opening section formed at the distal end, and connected to the suction unit, the control unit controls the operation of the suction unit, and when executing the discharge operation, the control unit causes the suction unit to operate as well.

According to this application example, it is possible to suck out, with the suction unit, via the suction opening section and the suction pipe, the fluid flowing out from the fluid ejecting unit to the stand during the predetermined discharge operation. Therefore, since it is unnecessary to separately provide a component for discharging the fluid flowing out to the stand, it is possible to simplify the structure of the stand.

APPLICATION EXAMPLE 6

This application example is directed to the fluid ejection device system according to the application example described above, wherein a plurality of the holding-information retaining sections are provided, the fluid ejecting unit includes a re-held state detecting unit for detecting whether the fluid ejecting unit is in a re-held state in which the fluid ejecting unit is held by the stand again, and when it is detected that the fluid ejecting unit is in the re-held state, the control unit causes the fluid supplying unit to operate for a predetermined second time under a predetermined second condition, under which the fluid having a flow rate smaller than a flow rate under the first condition is supplied, to thereby execute the discharge operation.

According to this application example, it is possible to more accurately discriminate, with the re-held-state detecting unit for detecting whether the fluid ejecting unit is in the re-held state in which the fluid ejecting unit is held by the stand again, whether the fluid ejecting unit is set for the first time or set again.

APPLICATION EXAMPLE 7

This application example is directed to the fluid ejection device system according to the application example described above, wherein the stand includes an insertion passage into which the fluid ejection pipe is inserted, a fluid accumulating section provided on the depth side of the insertion passage, the fluid flowing out from the fluid ejecting unit during the discharge operation being accumulated in the fluid accumulating section, and a sealing section configured to come into contact with the fluid ejecting unit to thereby seal a region including the fluid accumulating section, the nozzle, and the suction opening section when the fluid ejecting unit is held.

According to this application example, when the fluid ejecting unit is held by the stand, the region including the fluid accumulating section, the nozzle of the fluid ejecting unit, and the suction opening section is sealed. When the fluid flowing out from the fluid ejecting unit according to the predetermined discharge operation is sucked out by the suction unit, the region including the fluid accumulating section, the nozzle of the fluid ejecting unit, and the suction opening section develops negative pressure with a suction force of the suction unit. Therefore, when the predetermined discharge operation is performed, it is possible to perform the discharge operation using not only the fluid ejecting force of the fluid ejecting unit and the fluid feeding force of the fluid supplying unit but also the suction force of the suction unit.

APPLICATION EXAMPLE 8

This application example is directed to the fluid ejection device system according to the application example described above, wherein a stand-side suction unit configured to suck the fluid flowing out from the fluid ejecting unit according to the discharge operation is provided in the stand.

According to this application example, it is possible to suck out the fluid flowing out from the fluid ejecting unit by causing the stand-side suction unit to operate during the predetermined discharge operation. If the stand-side suction unit having a large suction force is provided, it is possible to powerfully suck out the fluid from the nozzle of the fluid ejecting unit by causing the stand-side suction unit to operate in the state in which the fluid ejecting unit is held by the stand. As a result, even when the nozzle is clogged, it is possible to eliminate the clogging. Even when the suction pipe is clogged like the nozzle, it is possible to eliminate the clogging.

APPLICATION EXAMPLE 9

This application example is directed to a medical apparatus including the fluid ejection device system explained above.

According to this application example, initial filling, air bubble discharge, and the like are performed without the operator adjusting a fluid ejection amount or the like while holding the fluid ejection device. Therefore, a burden on the operator is reduced and the operator can concentrate on treatment. Further, since air bubbles are discharged, it is possible to excise a biological tissue at desired depth.

BRIEF DESCRIPTION OF THE DRAWINGS

The invention will be described with reference to the accompanying drawings, wherein like numbers reference like elements.

DESCRIPTION OF EXEMPLARY EMBODIMENTS

In the following explanation, to clarify the contents of the invention explained above, an embodiment is explained according to order described below.
A. Device configuration
B. Fluid discharge processing
C. Modifications
C-1. First modification
C-2. Second modification

A. Device Configuration

Figure 1A:
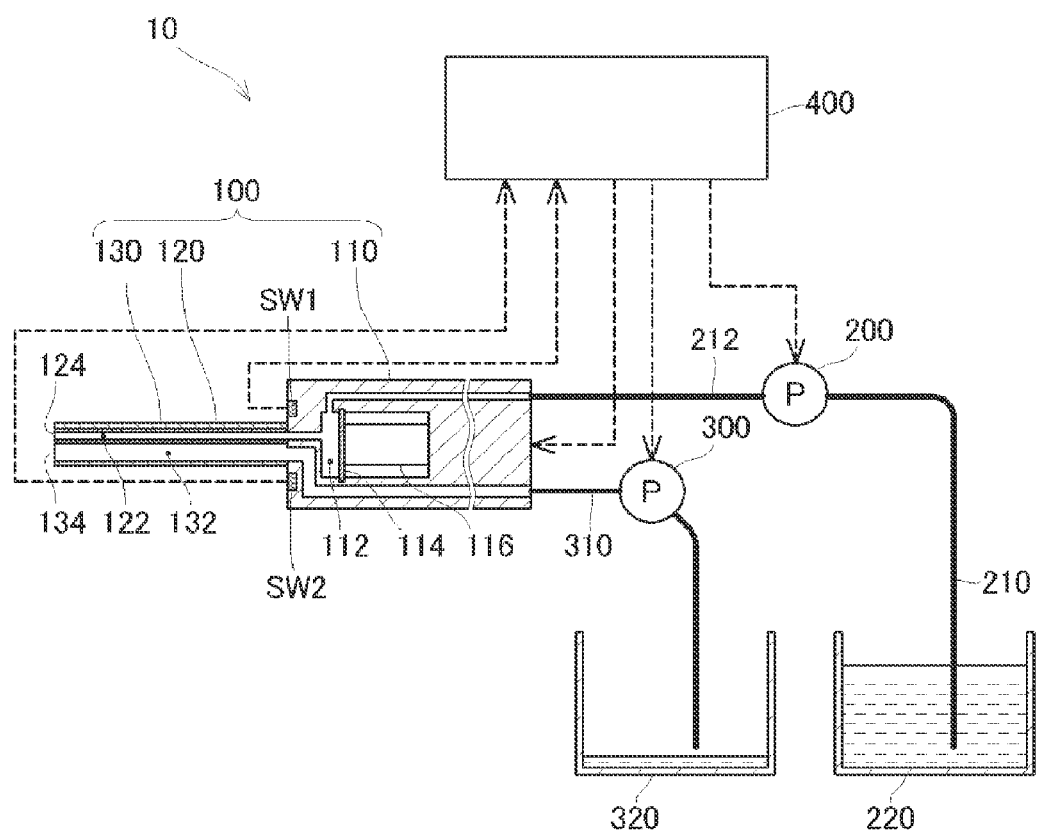
FIGS. 1A and 1B are explanatory diagrams showing a rough configuration of a fluid ejection device system in an embodiment.
Figure 1B:
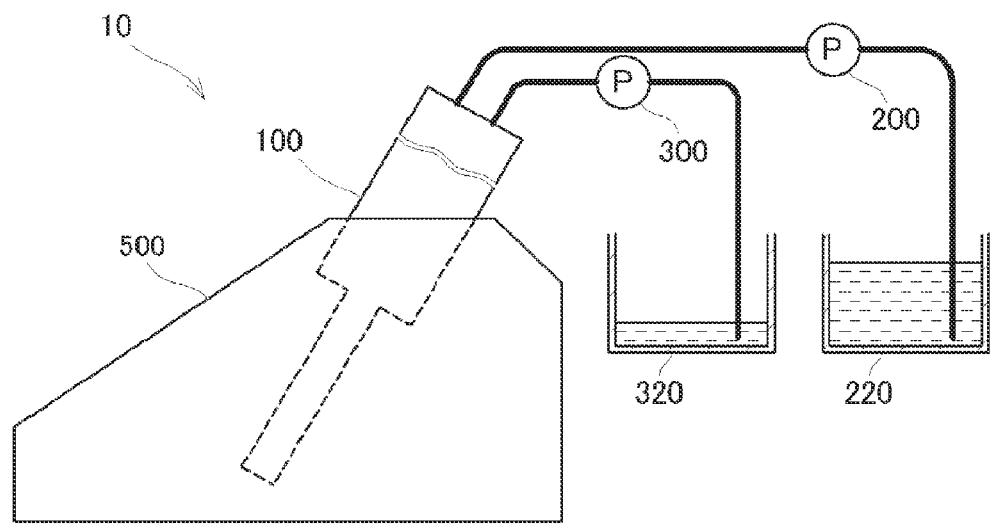

FIGS. 1A and 1B are explanatory diagrams showing a rough configuration of a fluid ejection device system 10 in this embodiment. The fluid ejection device system 10 shown in the figure is used for a surgical operation for ejecting fluid such as water or physiological saline to a biological tissue to incise or excise the biological tissue. As shown in FIG. 1A, the fluid ejection device system 10 in this embodiment includes a fluid ejection device 100 that an operator holds and operates to eject fluid, a fluid feeding pump 200 that supplies the fluid to the fluid ejection device 100, a fluid container 220 that stores the fluid to be ejected, a suction pump 300 that sucks the ejected fluid, a discharged fluid container 320 that stores the sucked fluid, and a control unit 400 that controls the operations of the fluid ejection device 100, the fluid feeding pump 200, and the suction pump 300. As shown in FIG. 1B, in the fluid ejection device system 10 in this embodiment, a stand 500 that holds the fluid ejection device 100 when the operator does not hold or operate the fluid ejection device 100 is provided. The fluid ejection device 100 in this embodiment corresponds to the "fluid ejecting unit" according to the application example of the invention. The fluid feeding pump 200 in this embodiment corresponds to the "fluid supplying unit" according to the application example of the invention. The suction pump 300 in this embodiment corresponds to the "suction unit" according to the application example of the invention.

The fluid ejection device 100 roughly includes a main body unit 110 and a fluid ejection pipe 120 and a suction pipe 130 erected in the main body unit 110. A nozzle 124 is formed at the distal end of the fluid ejection pipe 120. The nozzle 124 is connected to a fluid chamber 112 of the main body unit 110 via an ejection channel 122 of the fluid ejection pipe 120 and an internal channel of the main body unit 110. The fluid chamber 112 is connected to the fluid feeding pump 200 via the internal channel of the main body unit 110 and a second connection tube 212. The fluid feeding pump 200 is connected to the fluid container 220 via a first connection tube 210. The fluid feeding pump 200 supplies the fluid sucked up from the fluid container 220 to the fluid chamber 112 of the fluid ejection device 100 via the second connection tube 212. Apart of the fluid chamber 112 is configured by a diaphragm 114. A piezoelectric element 116 is provided while being set in contact with the diaphragm 114 from the outer side of the fluid chamber 112. As explained in detail below, when a driving signal is applied to the piezoelectric element 116, the fluid in the fluid chamber 112 is ejected from the nozzle 124 in a pulse-like manner.

The suction pipe 130 is a pipe having a diameter larger than the diameter of the fluid ejection pipe 120. The suction pipe 130 is provided in a state in which the fluid ejection pipe 120 is housed on the inner side of the suction pipe 130. A suction opening section 134 is formed at the distal end of the suction pipe 130. The suction opening section 134 is connected to the suction pump 300 via a suction channel 132 of the suction pipe 130, the internal channel of the main body unit 110, and a third connection tube 310. While the fluid is ejected from the nozzle 124 to a biological tissue, the fluid accumulated in a surgical site is sucked from the suction opening section 134 via the suction channel 132 by driving the suction pump 300.

In the fluid ejection device 100 in this embodiment, two switches (a first switch SW1 and a second switch SW2) are provided at an end of the main body unit 110 on a side where the fluid ejection pipe 120 and the suction pipe 130 are erected. Detection signals are output from the first switch SW1 and the second switch SW2 to the control unit 400. The control unit 400 can grasp states of the switches. A reason why the first switch SW1 and the second switch SW2 are provided is explained below.

Figure 2:
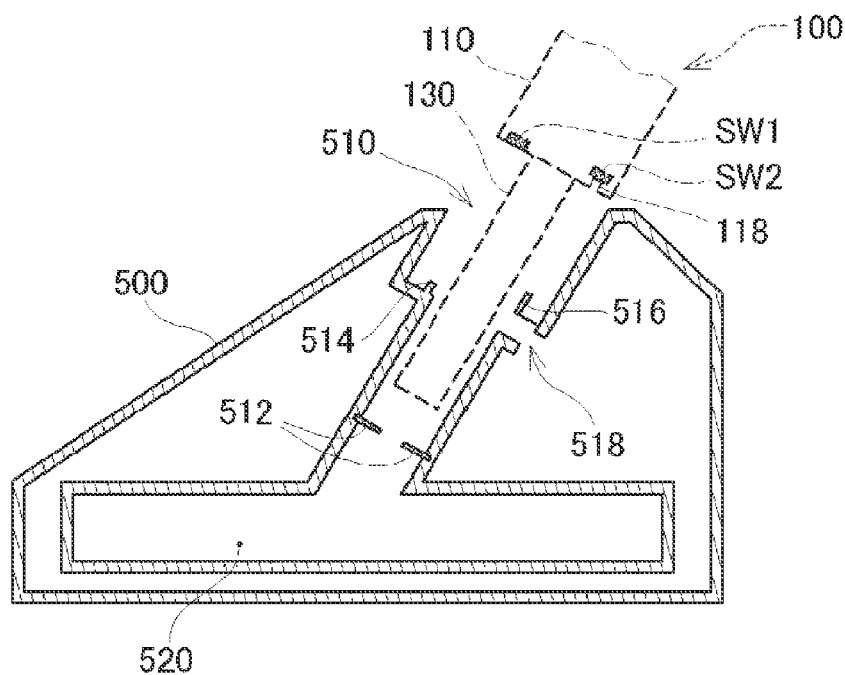
FIG. 2 is a sectional view showing detailed structure of a stand.

FIG. 2 is a sectional view showing detailed structure of the stand 500. In FIG. 2, the fluid ejection device 100 being set in the stand 500 is represented by a broken line.

As shown in the figure, an insertion passage 510 into which parts of the suction pipe 130 and the main body unit 110 of the fluid ejection device 100 are inserted is formed on the inside of the stand 500 in this embodiment. A space (a fluid accumulating section 520) for accumulating the fluid flowing out from the nozzle 124 of the fluid ejection device 100 is formed in a lower part (on the depth side) of the insertion passage 510. A seal section 512 made of rubber is provided on the inner wall of a portion of the insertion passage 510 into which the suction pipe 130 is inserted. When the suction pipe 130 is inserted, a gap between the outer circumference of the suction pipe 130 and the insertion passage 510 is closed by the seal section 512. The fluid accumulating section 520 is sealed up. The seal section 512 in this embodiment corresponds to the "sealing section" according to the application example of the invention.

In the portion of the insertion passage 510 into which the main body unit 110 is inserted, a projection 514 is provided in a position corresponding to the first switch SW1 of the fluid ejection device 100. A pin 516 is provided in a position corresponding to the second switch SW2 of the fluid ejection device 100. The pin 516 is coupled to the inner wall of the insertion passage 510 via a thin coupling member. In a position further on the lower side than the position where the pin 516 is coupled, a portion (a pierced section 518) where the inner wall of the insertion passage 510 is pierced is provided. In a position where the main body unit 110 of the fluid ejection device 100 is opposed to the tip of the pin 516, a communication path 118 having a diameter substantially the same as the diameter of the pin 516 is provided. The second switch SW2 is provided in the inner part of the communication path 118.

Figure 3A:
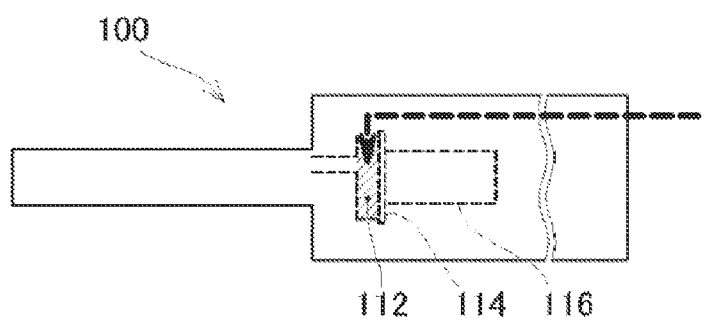
FIGS. 3A and 3B are explanatory diagrams showing an operation of a fluid ejection device for ejecting fluid.
Figure 3B:
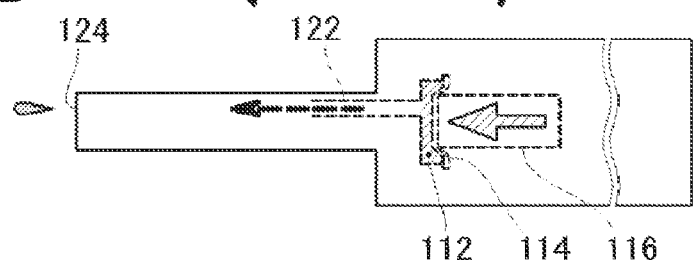

FIGS. 3A and 3B are explanatory diagrams showing an operation of the fluid ejection device 100 for ejecting the fluid. FIG. 3A represents a state in which, although the fluid feeding pump 200 that supplies the fluid to the fluid chamber 112 is driven, the piezoelectric element 116 is not driven (a state before a driving voltage is applied). In this state, as indicated by a thick broken line arrow in the figure, the fluid chamber 112 is filled with the fluid supplied from the fluid feeding pump 200. In the figure, a state in which the fluid chamber 112 is filled with the fluid is represented by hatching.

Subsequently, the piezoelectric element 116 is driven by applying the driving voltage. Then, the piezoelectric element 116 is deformed in an extending direction to deform the diaphragm 114 and reduce the volume of the fluid chamber 112. As a result, as shown in FIG. 3B, the fluid in the fluid chamber 112 is pressurized and ejected from the nozzle 124 via the ejection channel 122 in a pulse-like manner.

After the pulse-like fluid is ejected, the voltage applied to the piezoelectric element 116 is removed. Then, the deformed piezoelectric element 116 returns to the original length. Accordingly, the reduced volume of the fluid chamber 112 returns to the original volume. The fluid is supplied from the fluid feeding pump 200 to the fluid chamber 112 according to the increase in the volume of the fluid chamber 112. As a result, the fluid chamber 112 returns to the state before the piezoelectric element 116 is driven shown in FIG. 3A. When the driving voltage is applied to the piezoelectric element 116 again in this state, as shown in FIG. 3B, the piezoelectric element 116 is deformed and the fluid in the fluid chamber 112 is ejected from the nozzle 124 in a pulse-like manner. In this way, in the fluid ejection device system 10 in this embodiment, the fluid is ejected from the nozzle 124 in a pulse-like manner every time the driving voltage is applied to the piezoelectric element 116.

To eject the fluid from the nozzle 124 in a pulse-like manner as explained above, it is necessary to fill the fluid chamber 112 with the fluid. Therefore, when the use of the fluid ejection device 100 is started, work for filling the fluid chamber 112 with the fluid (initial filling work) is necessary. Thereafter, work for discharging air bubbles in the fluid chamber 112 (air bubble discharge work) is necessary as appropriate. If such work is complicated, the operator is burdened with the work. Therefore, in the fluid ejection device system 10 in this embodiment, processing explained below is performed to reduce the burden on the operator.

B. Fluid Discharge Processing

Figure 4:
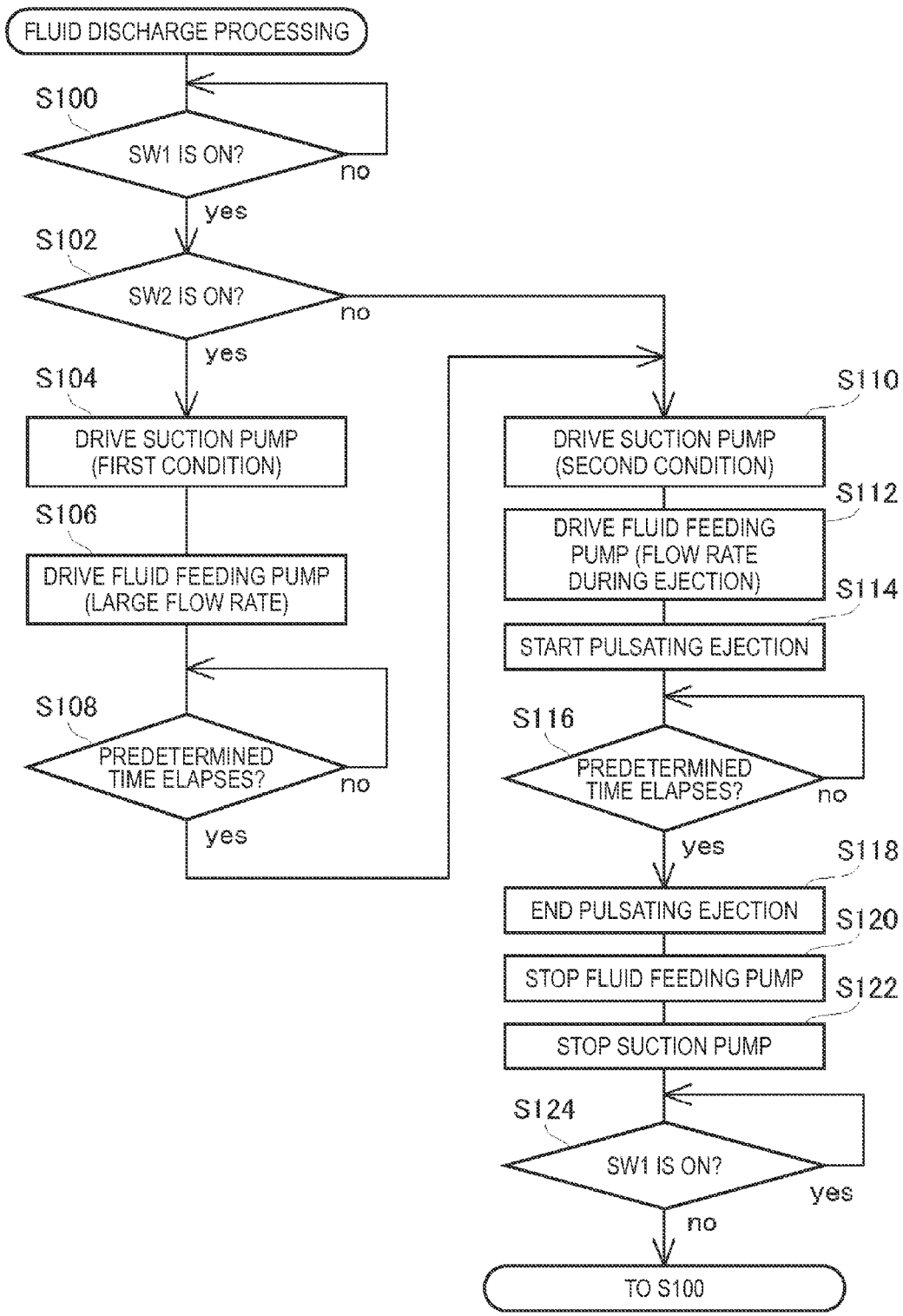
FIG. 4 is a flowchart for explaining fluid discharge processing executed by a control unit.

FIG. 4 is a flowchart of the fluid discharge processing executed by the control unit 400. The processing is started when the operator of the fluid ejection device system 10 starts the fluid ejection device system 10 and is executed until the operation of the fluid ejection device system 10 is ended. When the fluid discharge processing is started, first, the control unit 400 determines whether the first switch SW1 is on (step S100).

Figure 5A:
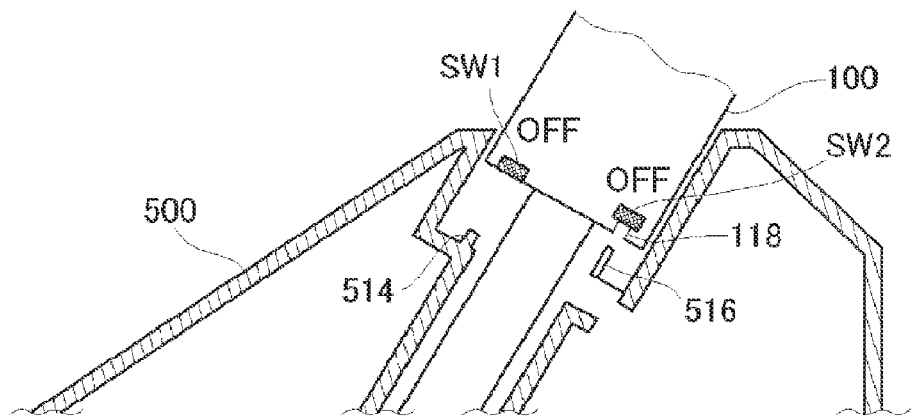
FIGS. 5A to 5C are explanatory diagrams showing a state in which a first switch is turned on when the fluid ejection device is set in the stand.
Figure 5B:
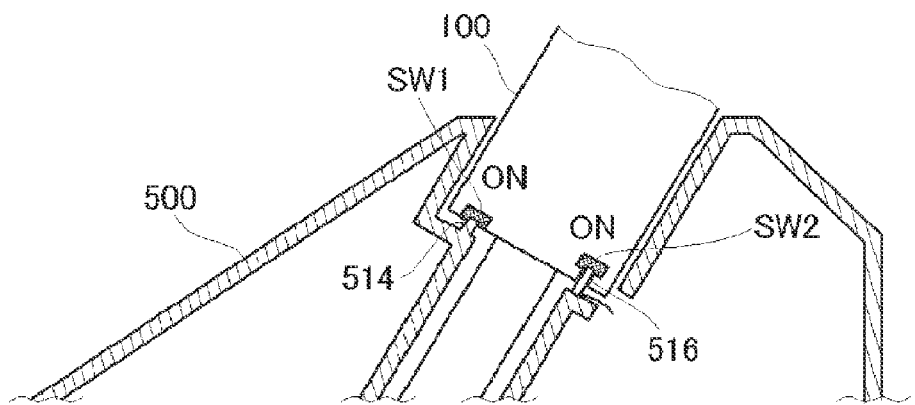
Figure 5C:
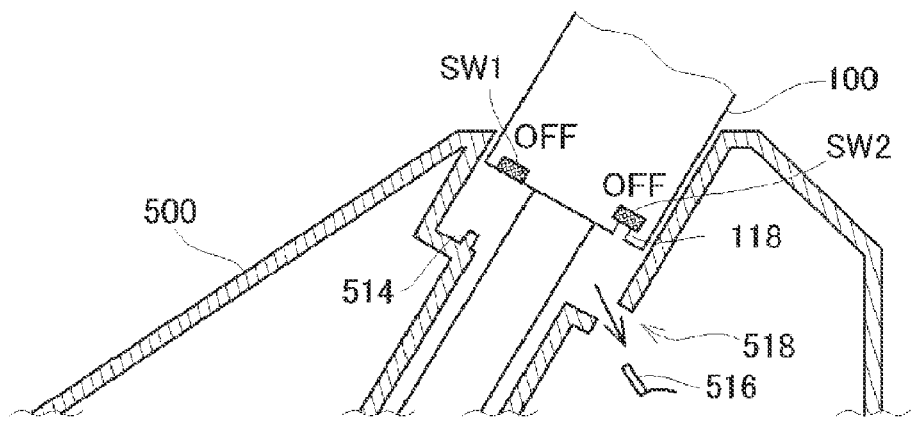

FIGS. 5A to 5C are explanatory diagrams showing a state in which the first switch SW1 is turned on when the fluid ejection device 100 is set in the stand 500. In FIGS. 5A to 5C, a state at the time when the fluid ejection device 100 is set in the stand 500 for the first time (hereinafter referred to as initial set time) is shown.

As shown in FIG. 5A, in the insertion passage 510 of the stand 500, the projection 514 is provided in the position corresponding to the first switch SW1 of the fluid ejection device 100. The pin 516 is provided in the position corresponding to the second switch SW2 of the fluid ejection device 100. Therefore, when the fluid ejection device 100 is set in the stand 500, as shown in FIG. 5B, the first switch SW1 is pushed by the projection 514 and turned on. The second switch SW2 is pushed by the tip of the pin 516, which is inserted through the communication path 118 of the fluid ejection device 100, and turned on.

Once the fluid ejection device 100 is set in the stand 500, the coupling member that couples the pin 516 and the inside wall of the insertion passage 510 is cut (see FIG. 5B). When the fluid ejection device 100 is detached from the stand 500 in this state, as shown in FIG. 5C, the pin 516 comes off the communication path 118 and drops from the pierced section 518. As a result, when the fluid ejection device 100 is set in the stand 500 again (hereinafter referred to as reset time), the second switch SW2 is not turned on and only the first switch SW1 is turned on.

In this embodiment, the pin 516 comes off the communication path 118. However, the pin 516 does not necessarily come off the communication path 118. The pin 516 may be pressed when the fluid ejection device 100 is set in the stand 500 and not return to a state before the pressing. In other words, the pin 516 only has to be configured such that, in a state in which the fluid ejection device 100 is set in the stand 500 for the first time, the first switch SW1 is turned on and the second switch SW2 is turned on and, when the fluid ejection device 100 is set again, the second switch SW2 is not turned on and only the first switch SW1 is turned on.

The first switch SW1 in this embodiment corresponds to the "held-state detecting unit" according to the application example of the invention. The second switch SW2 corresponds to the "initial-held-state detecting unit" according to the application example of the invention. The pin 516 in this embodiment corresponds to the "holding-information retaining section" according to the application example of the invention.

As explained above, the first switch SW1 of the fluid ejection device 100 is turned on when the fluid ejection device 100 is set in the stand 500 irrespective of whether the fluid ejection device 100 is set for the first time or set again. Therefore, in the fluid discharge processing in this embodiment shown in FIG. 4, after starting the processing, first, the control unit 400 determines whether the first switch SW1 is turned on to thereby determine whether the fluid ejection device 100 is set in the stand 500 (step S100). When determining that the first switch SW1 is on (the fluid ejection device 100 is set in the stand 500) (yes in step S100), the control unit 400 subsequently determines whether the second switch SW2 of the fluid ejection device 100 is on or off (step S102).

As explained above, the second switch SW2 of the fluid ejection device 100 is turned on only at the initial set time of the fluid ejection device 100 (see FIGS. 5A to 5C). Therefore, in the fluid discharge processing in this embodiment, when the first switch SW1 of the fluid ejection device 100 is on and the second switch SW2 is also on (yes in step S100 and yes in step S102), the control unit 400 determines that the current setting of the fluid ejection device 100 is the initial setting (the fluid chamber 112 of the fluid ejection device 100 is empty) and performs the initial filling work for the fluid chamber 112.

The control unit 400 performs the initial filling work by driving the fluid feeding pump 200 to supply the fluid to the fluid chamber 112 for a predetermined first time (in this embodiment, 30 seconds) at a large flow rate (in this embodiment, 30 ml per minute) equal to or larger than a flow rate used for treatment of a biological tissue. At this point, the fluid flows out from the nozzle 124 of the fluid ejection device 100 to the fluid accumulating section 520 of the stand 500.

In the initial filling work, first, the control unit 400 drives the suction pump 300 under a first condition (a suction amount: large) for the initial filling time (step S104). In this state, the control unit 400 drives the fluid feeding pump 200 to supply the fluid to the fluid chamber 112 at the large flow rate (step S106). In the fluid accumulating section 520, only an insertion place for the fluid ejection device 100 is formed as an opening section. Therefore, since the fluid flowing out to the fluid accumulating section 520 is sucked out from the suction opening section 134, the fluid does not overflow from the stand 500. The control unit 400 continues the supply of the fluid before the predetermined first time elapses from the start of the supply of the fluid to the fluid chamber 112 (no in step S108). When the predetermined first time elapses (yes in step S108), the control unit 400 determines that the initial filling work is completed and performs the fluid discharge work for the fluid chamber 112.

The control unit 400 performs the fluid discharge work by ejecting the fluid from the nozzle 124 in a pulse-like manner (pulsating ejection) for a predetermined second time. Therefore, the control unit 400 changes the driving condition for the suction pump 300 to a second condition (a suction amount: medium) for fluid discharge time (step S110), changes the fluid flow rate of the fluid feeding pump 200 to a flow rate during ejection (in this embodiment, 10 ml per minute) (step S112), and starts the pulsating ejection by applying the driving voltage to the piezoelectric element 116 (step S114). The initial filling work is performed in a preparatory period until the start of the use of the fluid ejection device 100. The fluid flow rate of the fluid feeding pump 200 is set large to shorten the preparatory period. On the other hand, in the fluid discharge work for discharging air bubbles, the fluid flow rate of the fluid feeding pump 200 is set smaller than the flow rate during the initial filling work. When the fluid flow rate of the fluid feeding pump 200 is large, the flow velocity of the fluid on the inside of the fluid ejection device 100 increases. Air bubbles adhere to ends and the like on the inside of the fluid ejection device 100. The air bubbles are sometimes not discharged from the fluid ejection device 100. Therefore, the fluid flow rate of the fluid feeding pump 200 is set smaller than the flow rate during the initial filling work. Consequently, it is possible to discharge the air bubbles at the ends and the like on the inside of the fluid ejection device 100. Since the suction pump 300 is driving even while the pulsating ejection is performed, the fluid ejected to the fluid accumulating section 520 is sucked out from the suction opening section 134. In this way, the control unit 400 continues the pulsating ejection before the predetermined time elapses from the start of the pulsating ejection (no in step S116) and, when the predetermined time elapses (yes in step S116), ends the pulsating ejection (step S118), stops the fluid feeding pump 200 and the suction pump 300 (steps S120 and S122), and ends the fluid discharge work.

After ending the fluid discharge work, the control unit 400 determines whether the first switch SW1 of the fluid ejection device 100 is on (step S124). If the fluid ejection device 100 is kept setting in the stand 500, the control unit 400 determines that the first switch SW1 is on (yes in step S124) and stays on standby. Then, when the fluid ejection device 100 is detached from the stand 500 and the first switch SW1 is turned off (no in step S124), the control unit 400 returns to the start of the fluid discharge processing and determines whether the fluid ejection device 100 is set in the stand 500 again (step S100).

When the fluid ejection device 100 is set in the stand 500 again, the first switch SW1 is turned on (yes in step S100). However, since the pin 516 for turning on the second switch SW2 has already come off, the second switch SW2 is kept off (no in step S102). In this case, the control unit 400 does not perform the initial filling work (steps S104, S106, and S108). The control unit 400 drives the suction pump 300 under the second condition during the fluid discharge for discharging air bubbles (step S110) and, while driving the fluid feeding pump 200 to supply the fluid to the fluid chamber 112 (step S112), starts the pulsating ejection (step S114) to perform the fluid discharge work for discharging air bubbles. When the predetermined time elapses from the start of the pulsating ejection (yes in step S116), the control unit 400 ends the pulsating ejection (step S118), stops the fluid feeding pump 200 and the suction pump 300 (steps S120 and S122), and stays on standby until the fluid ejection device 100 is detached from the stand 500 (until the first switch SW1 is turned off). When the first switch SW1 of the fluid ejection device 100 is turned off (no in step S124), the control unit 400 returns to the start of the fluid discharge processing. Thereafter, the control unit 400 repeats the same processing until the operation of the fluid ejection device system 10 ends.

As explained above, in the fluid ejection device system 10 in this embodiment, the initial filling work and the fluid discharge work for discharging air bubbles can be automatically performed simply by setting the fluid ejection device 100 in the stand 500. Therefore, since the operator does not need to manually perform these kinds of work, it is possible to reduce a burden on the operator. If the fluid ejection device 100 is set in the stand 500 when the operator does not hold or operate the fluid ejection device 100, the fluid discharge work for discharging air bubbles is performed while the fluid ejection device 100 is set in the stand 500. Therefore, when the operator resumes the operation of the fluid ejection device 100, it is possible to resume the operation in a satisfactory state (a state in which air bubbles in the fluid chamber are discharged).

The fluid flowing out to the fluid accumulating section 520 of the stand 500 from the nozzle 124 when the initial filling work and the fluid discharge work for discharging air bubbles are performed is sucked out by the suction pump 300 connected to the fluid ejection device 100. Therefore, since a passage or the like for discharging the fluid accumulated in the fluid accumulating section 520 to the outside does not have to be provided in the stand 500, it is possible to simplify the structure of the stand 500. Further, as explained above with reference to FIG. 2, in the state in which the fluid ejection device 100 is set in the stand 500, the gap between the outer circumference of the suction pipe 130 and the insertion passage 510 of the stand 500 is closed by the seal section 512. The fluid accumulating section 520 is sealed up. When the initial filling work and the fluid discharge work for discharging air bubbles are performed in this state, negative pressure is developed in the fluid accumulating section 520 by the suction force of the suction pump 300. The fluid is sucked out from the nozzle 124 to the fluid accumulating section 520 by the negative pressure. Therefore, it is possible to perform the initial filling work and the fluid discharge work for discharging air bubbles using not only the fluid ejecting force of the fluid ejection device 100 and the fluid pumping pressure of the fluid feeding pump 200 but also the suction force of the suction pump 300.

In addition, in the fluid ejection device system 10 in this embodiment, it is possible to perform the initial filling work for the fluid chamber 112 only when the fluid ejection device 100 is set in the stand 500 for the first time. Therefore, when the initial filling work is performed (when the use of the fluid ejection device 100 is started), it is necessary to prepare the stand 500 not used yet. Therefore, since the fluid ejection device 100 is suppressed from being set in the stand 500 already used, it is possible to keep the fluid ejection device 100 sanitary. Therefore, it is suitable to use the fluid ejection device system 10 in this embodiment as a medical apparatus from the viewpoint of infection prevention.

C. Modifications

There are various modifications of the fluid ejection device system 10 in this embodiment explained above. The modifications are briefly explained below. In the following explanation of the modifications, differences from the fluid ejection device system 10 in this embodiment are mainly explained. Components same as the components of the fluid ejection device system 10 in this embodiment are denoted by the same reference numerals and signs and explanation of the components is omitted.

C-1. First Modification

In the explanation of the fluid ejection device system 10 in this embodiment, the pin 516 is provided in the stand 500 and the presence or absence of the pin 516 is detected with the second switch SW2 of the fluid ejection device 100, whereby it is determined whether the fluid ejection device 100 is set in the stand 500 for the first time. As a method of determining whether the fluid ejection device 100 is set in the stand 500 for the first time, for example, a method explained below can also be used.

Figure 6A:
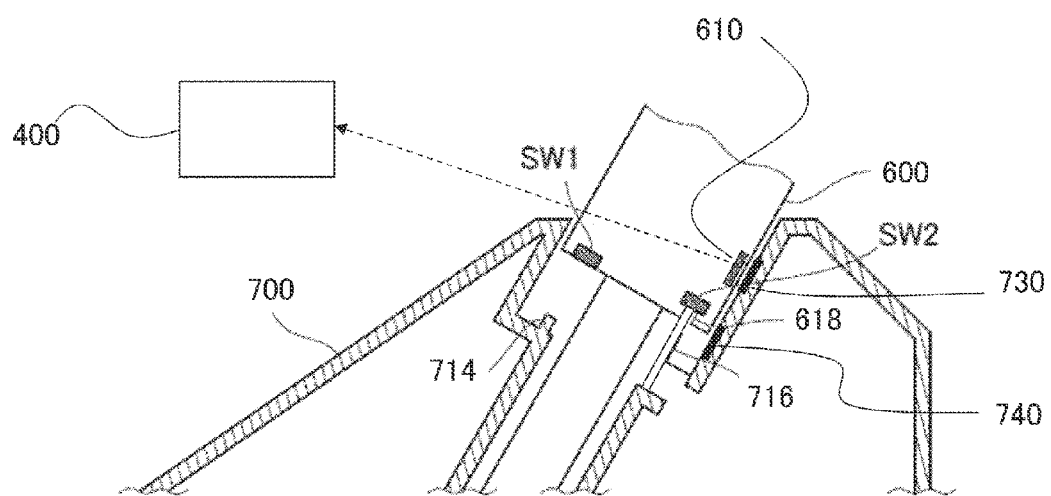
FIGS. 6A and 6B are explanatory diagrams showing a state in which a fluid ejection device in a first modification is set in a stand.
Figure 6B:
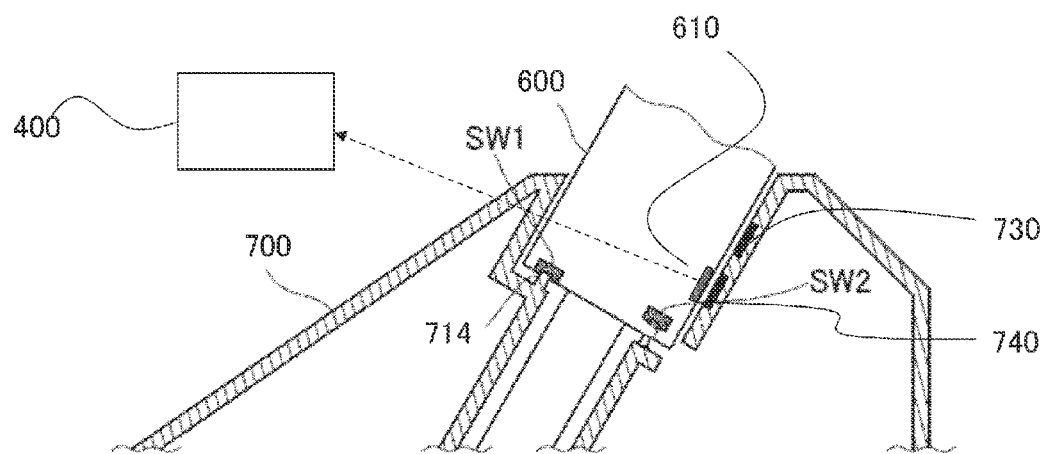

FIGS. 6A and 6B are explanatory diagrams showing a state in which a fluid ejection device in a first modification is set in a stand 700.

As shown in FIG. 6A, a first difference from the configuration shown in FIG. 2 is that a pin 716 is long compared with the pin 516 shown in FIG. 2. Therefore, when a fluid ejection device 600 is set in the stand 700 for the first time, as shown in FIG. 6A, the second switch SW2 of the fluid ejection device 600 is pushed by the tip of the pin 716 inserted through a communication path 618 and is turned on. At this point, unlike the structure shown in FIG. 2, since the pin 716 is long, the first switch SW1 is not turned on. The pin 716 comes off when the fluid ejection device 600 is detached from the stand 700 at the initial set time as in the fluid ejection device system 10 in this embodiment. At the reset time, since the pin 716 of the stand 700 has already come off, the fluid ejection device 600 is inserted into a position deeper than a position at the initial set time as shown in FIG. 6B. Only the first switch SW1 is pushed by a projection 714 and turned on. The pin 716 in this modification corresponds to the "re-held-state detecting unit" according to the application example of the invention.

As explained above, the second switch SW2 is turned on at the initial set time and the first switch SW1 is turned on at the reset time. Therefore, the control unit 400 can discriminate whether the fluid ejection device 600 is set for the first time or set again.

A second difference is that a first ID display section 730 and a second ID display section 740 assigned with IDs are provided in the stand 700. In the fluid ejection device 600, a reading unit 610 that reads the IDs is provided in a position corresponding to the first ID display section 730 of the stand 700 when the fluid ejection device 600 is set in the stand 700 for the first time.

The fluid ejection device 600 is set in the position shown in FIG. 6A at the initial set time. Therefore, the reading unit 610 can read the ID of the first ID display section 730. The reading unit 610 sends the ID to the control unit 400 and causes the control unit 400 to store the ID. On the other hand, at the reset time, the pin 716 comes off and the fluid ejection device 600 is inserted into the position of the stand 700 deeper than the position at the initial set time. Therefore, the reading unit 610 reads the ID of the second ID display section 740. As at the initial set time, the reading unit 610 sends the ID of the second ID display section 740 to the control unit 400. Different IDs are respectively assigned to the first ID display section 730 and the second ID display section 740. Therefore, the control unit 400 can also determine, according to a difference of a read-out ID, whether the fluid ejection device 600 is set for the first time or set again.

With the configuration explained above, even when the pin 716 does not come off after the initial set time or when the pin 716 has already come off before the initial setting time, it is possible to check, by identifying the ID, whether the fluid ejection device 600 is set in the stand 700 for the first time. In other words, when the ID of the first ID display section 730 is read out a plurality of times or when the ID of the first ID display section 730 is not read out at all and the ID of the second ID display section 740 is read out, it is possible to determine that the pin 716 fails to function because of some reason. Therefore, it is possible to more accurately discriminate whether the fluid ejection device 600 is set for the first time or set again.

C-2. Second Modification

In the explanation of the fluid ejection device system 10 in this embodiment, the fluid flowing out to the fluid accumulating section 520 of the stand 500 during the initial filling work or the fluid discharge work for discharging air bubbles of the fluid discharge processing is sucked using the suction pump 300 connected to the fluid ejection device 100. A suction pump exclusive for the stand 500 may be provided for the purpose of sucking the fluid flowing out to the fluid accumulating section 520 during the initial filling work or the fluid discharge work for discharging air bubbles.

Figure 7:
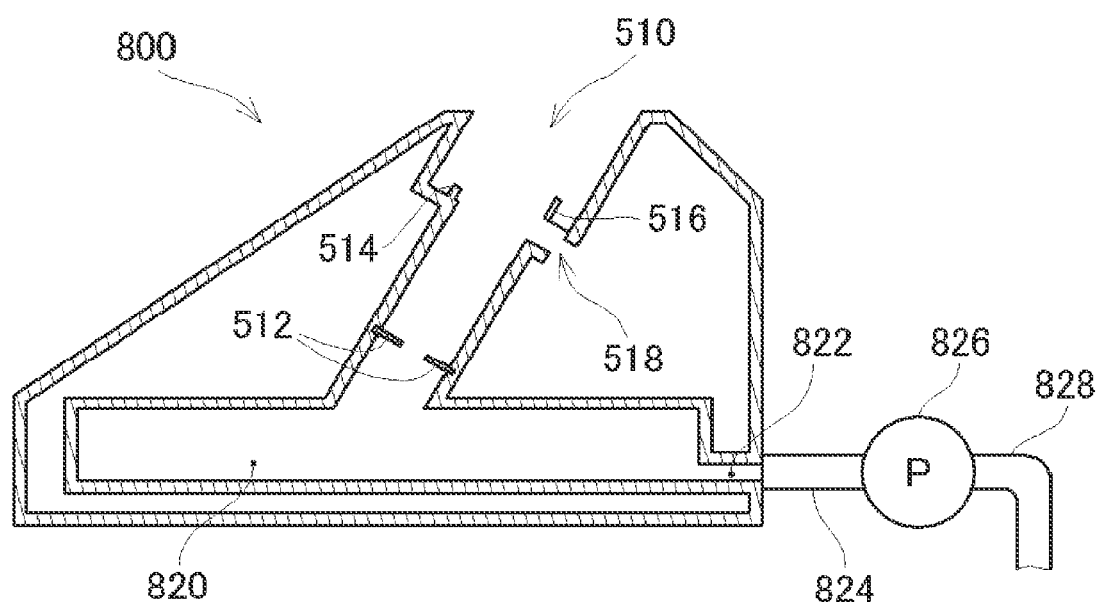
FIG. 7 is a sectional view showing the structure of a stand in a second modification.

FIG. 7 is a sectional view showing the structure of the stand 800 in a second modification. As shown in the figure, a fluid accumulating section 820 of a stand 800 in this modification is connected to a stand-side suction pump 826 via a discharge passage 822 and a first fluid discharge tube 824. The stand-side suction pump 826 is connected, via a second fluid discharge tube 828, to the discharged fluid container 320 (see FIGS. 1A and 1B) in which the fluid sucked by the suction pump 300 on the fluid ejection device 100 side is stored. The stand-side suction pump 826 in this modification corresponds to the "stand-side suction unit" according to the application example of the invention.

If the stand-side suction pump 826 is provided in the stand 800 in this way, it is possible to suck, using the stand-side suction pump 826, the fluid flowing out to the fluid accumulating section 820 during the initial filling work or the fluid discharge work for discharging air bubbles. If the stand-side suction pump 826 is driven in a state in which the fluid ejection device 100 is inserted into the stand 800, it is possible to generate negative pressure larger than the negative pressure generated by the suction pump 300 connected to the fluid ejection device 100 and suck out the fluid from the nozzle 124. Therefore, even when the nozzle 124 is clogged, it is possible to eliminate the clogging.

The fluid ejection device system according to the application example of the invention is explained above with reference to the embodiment. However, the invention is not limited to the embodiments. The invention can be carried out in various forms without departing from the spirit of the invention. For example, the volume of the fluid chamber 112 may be changed by a piston instead of the diaphragm 114. The fluid may be ejected by the pressure of the fluid feeding pump 200 without using the diaphragm 114 or the fluid chamber 112. The fluid ejection is not limited to the pulsating ejection and may be continuous flow ejection. In the embodiment, the fluid discharge work is explained as the fluid discharge work for discharging air bubbles. However, the fluid discharge work may be fluid discharge work for preventing solidification of the tip of the nozzle 124.

This application claims priority to Japanese Patent Application No. 2012-032462, filed on Feb. 17, 2012, and Application No. 2012-087125, filed on Apr. 6, 2012, the entirety of which are hereby incorporated by reference.

What is claimed is:

1. A medical apparatus comprising:
a fluid ejecting unit having a body with a fluid ejection pipe and a suction pipe extending from the body, a nozzle being disposed at a distal end the fluid ejection pipe, the nozzle being configured to eject fluid from the fluid ejecting unit, the fluid ejection pipe being disposed within the suction pipe;
a fluid supplying unit configured to supply fluid to the fluid ejecting unit;
a control unit configured to control operation of the fluid ejecting unit and the fluid supplying unit; and
a stand configured to hold the fluid ejection pipe and at least a portion of the body of the fluid ejecting unit within the stand, the stand including an insertion passage that the fluid ejection pipe and the suction pipe are inserted and a fluid accumulating section where fluid discharged from the nozzle is temporarily accumulated before being removed through the suction pipe, wherein slidable engagement of the stand with the fluid ejecting unit changes an operational state of the fluid ejecting unit,
the control unit discharges fluid from the nozzle by driving the fluid supplying unit when the fluid ejecting unit is held by the stand.

2. The medical apparatus according to claim 1, wherein the control unit executes a first discharge operation that discharge fluid from the nozzle by supplying fluid at a first flow rate from the fluid supplying unit to the fluid ejecting unit.

3. The medical apparatus according to claim 2, wherein the control unit executes a second discharge operation that discharges fluid from the nozzle by supplying fluid at a second flow late smaller than the first flow late from the supplying unit to the fluid ejecting unit.

4. The medical apparatus according to claim 3, wherein the control unit executes the first discharge operation and the second discharge operation when the fluid ejecting unit is held by the stand.

5. The medical apparatus according to claim 4, wherein the control unit executes the first discharge operation during an initial-held-state where the fluid ejecting unit is held by the stand for the first time.

6. The medical apparatus according to claim 5, wherein the control unit executes the second discharge operation after the first discharge operation is executed.

7. The medical apparatus according to claim 1, further comprising:

a first suction unit configured to suck fluid discharged from the nozzle; and
the suction pipe having a suction opening and configured to connect to the first suction unit, wherein
the control unit discharges fluid from the nozzle by driving the fluid supplying unit in a state where the first suction unit is driven.

8. The medical apparatus according to claim 7, wherein the stand includes:
a sealing portion configured to seal a region including the fluid accumulating section, the nozzle and the suction opening when the fluid ejecting pipe and the suction pipe are inserted.

9. A fluid discharging method of a medical apparatus having (i) a fluid ejecting unit having a body with a fluid ejection pipe and a suction pipe extending from the body, a nozzle being disposed at a distal end the fluid ejection pipe, the nozzle being configured to eject fluid from the fluid ejecting unit, the fluid ejection pipe being disposed within the suction pipe, (ii) a fluid supplying unit configured to supply fluid to the fluid ejecting unit; (iii) a control unit configured to control operation of the fluid ejecting unit and the fluid supplying unit; and (iv) a stand configured to hold the fluid ejection pipe and at least a portion of the body of the fluid ejecting unit within the stand, the stand including an insertion passage that the fluid ejecting pipe and the suction pipe being are inserted and a fluid accumulating section where fluid discharged from the nozzle is temporarily accumulated before being removed through the suction pipe, wherein slidable engagement of the stand with the fluid ejecting unit changes an operational state of the fluid ejecting unit, the control unit is configured to discharge fluid from the nozzle by driving the fluid supplying unit when the fluid ejecting unit is held by the stand, the method comprising:
discharging fluid from the fluid ejecting unit by driving the fluid supplying unit in a state where the fluid ejecting unit is held by the stand, the stand including an insertion passage that a fluid ejecting pipe and an suction pipe of the fluid ejecting unit are inserted and a fluid accumulating section where fluid discharged from the nozzle is temporarily accumulated before being removed through the suction pipe, the fluid ejecting pipe and the suction pipe extending from a body of the fluid ejecting unit, with the fluid ejecting pipe being disposed within the suction pipe, and slidable engagement of the stand with the fluid ejecting unit changing an operational state of the fluid ejecting unit.

10. The fluid discharging method according to claim 9, wherein
discharging fluid from the fluid ejecting unit occurs by supplying fluid at a first flow rate from the fluid supplying unit to the fluid ejecting unit, and
discharging fluid from the fluid ejecting unit occurs by supplying fluid at a second flow late smaller than the first flow rate from the supplying unit to the fluid ejecting unit.

11. The fluid discharging method according to claim 10, wherein
discharging fluid from the fluid ejecting unit occurs by supplying fluid at the first flow rate from the fluid supplying unit to the fluid ejecting unit when the fluid ejecting unit is held by the stand for the first time.

12. The fluid discharging method according to claim 9, further comprising:

determining that the fluid ejecting unit is held by the stand.

\* \* \* \* \*